(12) United States Patent
Horton, III

(10) Patent No.: US 6,524,529 B1
(45) Date of Patent: *Feb. 25, 2003

(54) APPLIANCES HAVING UV DISINFECTION DEVICE AND METHOD

(76) Inventor: Isaac B. Horton, III, 8824 Stage Ford Rd., Raleigh, NC (US) 27615

( * ) Notice: Subject to any disclaimer, the term of this patent is extended or adjusted under 35 U.S.C. 154(b) by 22 days.

This patent is subject to a terminal disclaimer.

(21) Appl. No.: 09/724,180

(22) Filed: Nov. 28, 2000

(51) Int. Cl.⁷ .................................................. A61L 9/00
(52) U.S. Cl. ........................ 422/24; 210/636; 210/748; 385/147; 250/450.11
(58) Field of Search .................. 385/147; 210/636, 210/748; 422/24; 250/450.11

(56) References Cited

U.S. PATENT DOCUMENTS

| | | | |
|---|---|---|---|
| 4,103,167 A | * 7/1978 | Ellner | 250/365 |
| 4,755,292 A | * 7/1988 | Merriam | 210/192 |
| 5,780,860 A | 7/1998 | Gadgil et al. | |
| 5,992,684 A | 11/1999 | Russell | |
| 6,027,766 A | 2/2000 | Greenberg et al. | |
| 6,090,296 A | 7/2000 | Oster | |
| 6,094,767 A | * 8/2000 | Iimura | 15/105 |
| 6,103,363 A | 8/2000 | Boire et al. | |
| 6,110,528 A | 8/2000 | Kimura et al. | |
| 6,117,337 A | 9/2000 | Gonzalez-Martin et al. | |
| 6,403,030 B1 | * 6/2002 | Horton, III | 210/748 |

* cited by examiner

Primary Examiner—Robert H. Kim
Assistant Examiner—George Wang
(74) Attorney, Agent, or Firm—Glasgow Law Firm, PLLC

(57) ABSTRACT

An ultraviolet disinfection (UV) system for appliances including at least one UV light-ready appliance having at least one portal in the appliance for receiving UV light input from at least one light source, which is removably connected to the at least one UV light-ready appliance via a connector at the portal, and positioned to provide a focused, controllable UV light output that has at least one UV dose zone for providing effective sterilization of microorganisms and disinfection within an interior of the appliance. Also, an ultraviolet disinfection (UV) system for appliances, the system comprising at least one light source positioned within a housing that is external to at least one appliance and capable of being connected thereto via at least one connector and connected to a power source for producing a UV light output from the housing; this system includes at least one source optical component positioned between the at least one light source and the UV light output from the housing, thereby producing a focused, controllable UV light output that has at least one UV dose zone for providing effective sterilization of microorganisms within the at least one appliance. A method for UV disinfection of the interior of appliances is also included in the present invention.

50 Claims, 1 Drawing Sheet

APPLIANCES HAVING UV DISINFECTION DEVICE AND METHOD

BACKGROUND OF THE INVENTION (1) Field of the Invention

The present invention relates generally to a system and method for ultraviolet disinfection and, more particularly, to a system and method for ultraviolet disinfection of appliances.

(2) Description of the Prior Art

UV Mechanism of Action

It is well known in the art to use ultraviolet light (UV) for the disinfection treatment of water. Ultraviolet light, at the germicidal wavelength of 253.7 nanometers, alters the genetic (DNA) material in cells so that bacteria, viruses, molds, algae and other microorganisms can no longer reproduce. The microorganisms are considered dead, and the risk of disease from them is eliminated. As the water flows past the UV lamps in UV disinfection systems, the microorganisms are exposed to a lethal dose of UV energy. UV dose is measured as the product of UV light intensity times the exposure time within the UV lamp array. Microbiologists have determined the effective dose of UV energy to be approximately about 34,000 microwatt-seconds/cm2 needed to destroy pathogens as well as indicator organisms found in wastewater. Typical prior art disinfection systems and devices emit UV light at approximately 254 nm, which penetrates the outer cell membrane of microorganisms, passes through the cell body, reaches the DNA and alters the genetic material of the microorganism, destroying it without chemicals by rendering it unable to reproduce.

Ultraviolet light is classified into three wavelength ranges: UV-C, from about 200 nanometers (nm) to about 280 nm; UV-B, from about 280 nm to about 315 nm; and UV-A, from about 315 nm to about 400 nm. Generally, UV light, and in particular, UV-C light is "germicidal," i.e., it deactivates the DNA of bacteria, viruses and other pathogens and thus destroys their ability to multiply and cause disease, effectively resulting in sterilization of the microorganisms. Specifically, UV "C" light causes damage to the nucleic acid of microorganisms by forming covalent bonds between certain adjacent bases in the DNA. The formation of these bonds prevents the DNA from being "unzipped" for replication, and the organism is neither able to produce molecules essential for life process, nor is it able to reproduce. In fact, when an organism is unable to produce these essential molecules or is unable to replicate, it dies. UV light with a wavelength of approximately between about 250 to about 260 nm provides the highest germicidal effectiveness. While susceptibility to UV light varies, exposure to UV energy for about 20 to about 34 milliwatt-seconds/cm$^2$ is adequate to deactivate approximately 99 percent of the pathogens.

Regulation of Drinking Water Standards

Exposure to pathogens does not always cause disease; whether drinking contaminated water could produce disease depends on the type and quantity of pathogen ingested and the health (nutritional and immunological) status of the person ingesting the pathogen. However, the use of low-level antibiotics to improve feed conversion in domestic animals has led to the emergence of antibiotic-resistant pathogens. In recognition of this problem, US governmental agencies are seeking to improve the control of food production through such programs as the Hazard Analysis Critical Control Point (HACCP). Additionally, the manufacturers of detergents have started incorporating disinfectants in their products in order to supply persons with a more effective means to control these pathogens. Unfortunately, these disinfectants leave residues on appliance surfaces. Persons unfamiliar with the chemistry of these disinfectants may desire a chemical-free means to disinfect their appliances.

The most common means of maintaining water used in household appliances at an acceptable purity for long periods of time is through the addition of reactive chlorine. Unfortunately, evidence is mounting that organic chemical byproducts of chemical disinfection, especially byproduct of chlorination such as dioxane, are carcinogens and/or toxins for humans. Therefore, chemical disinfection is not a viable alternative when chemical purity of the fluid is desired and/or required. Additionally, in spite of this toxicological evidence, the EPA has recently been forced to relax restrictions on certain known carcinogenic chlorination by-product, such as chloroform. Additionally, other chemicals, such as the nitrate ion, have been shown to negatively influence the development of children.

In light of the emerging data concerning the toxicity of organic and inorganic chemicals and the relaxation of water purity regulations, persons interested in maintaining their health have been pursuing the supply of chemically pure water. Generation of such water requires filtration to remove the chemicals. Unfortunately, systems based on filtration require frequent replacement and/or cleaning of filters. In addition, storage of such water requires a system to maintain sterility for extended periods of time. Thus, there exists a need for a system that can easily remove or eliminate organic compounds from drinking water and maintain the sterility of that water during storage. No prior art systems for the disinfection of appliances through UV light are known.

Thus, there remains a need for a UV disinfection system for treating appliances Additionally, there remains a need for a appliance sterilization system that can easily accommodate new appliances into the UV disinfection system.

SUMMARY OF THE INVENTION

The present invention is directed to a UV disinfection system and method for treating appliances.

One object of the present invention is to provide a UV-ready appliance that is designed to accept a UV light source input for the purpose of sterilization of the interior of a variety of appliances, including any and all objects, fluids, materials, and surfaces contained within the interior of the appliances, albeit temporarily.

Another object of the present invention is to provide a UV disinfection system for treating the interior of appliances configured and arranged to function effectively with at least one UV light source or lamp.

Another object of the present invention includes presentation of the UV light source in at least two primary configurations: (1) attached to the appliance, and (2) detached from and remotely connectable with the appliance via fiber optic, UV transmission lines.

Still another object of the present invention is to provide a method for providing ultraviolet disinfection (UV) within appliances including selective activation and deactivation of at least one UV light-ready appliance having at least one portal in the appliance for receiving UV light input from at least one light source, which is removably connected to the at least one UV light-ready appliance via a connector at the portal, and provides a focused, controllable UV light output that has at least one UV dose zone for providing effective sterilization of microorganisms and disinfection within an interior of the appliance.

Accordingly, one aspect of the present invention is to provide a UV-ready appliance that is designed to accept a UV light source input for the purpose of sterilization of the interior of a variety of appliances, including any and all objects, fluids, materials, and surfaces contained within the interior of the appliances, albeit temporarily.

Another aspect of the present invention is to provide a UV disinfection system for treating appliances configured and arranged to function effectively with at least one UV light source or lamp.

Still another aspect of the present invention is to includes presentation of the UV light source in at least two primary configurations: (1) attached to the appliance, and (2) detached from and remotely connectable with the appliance via fiber optic, UV transmission lines and including the use of optical components.

Yet another aspect of the present invention is to provide a method for providing ultraviolet disinfection (UV) within appliances including selective activation and deactivation of at least one UV light-ready appliance having at least one portal in the appliance for receiving UV light input from at least one light source, which is removably connected to the at least one UV light-ready appliance via a connector at the portal, and provides a focused, controllable UV light output that has at least one UV dose zone for providing effective sterilization of microorganisms and disinfection within an interior of the appliance.

These and other aspects of the present invention will become apparent to those skilled in the art after a reading of the following description of the preferred embodiment according to the present invention when considered with the drawings.

DETAILED DESCRIPTION OF THE PREFERRED EMBODIMENTS

Figure 1:
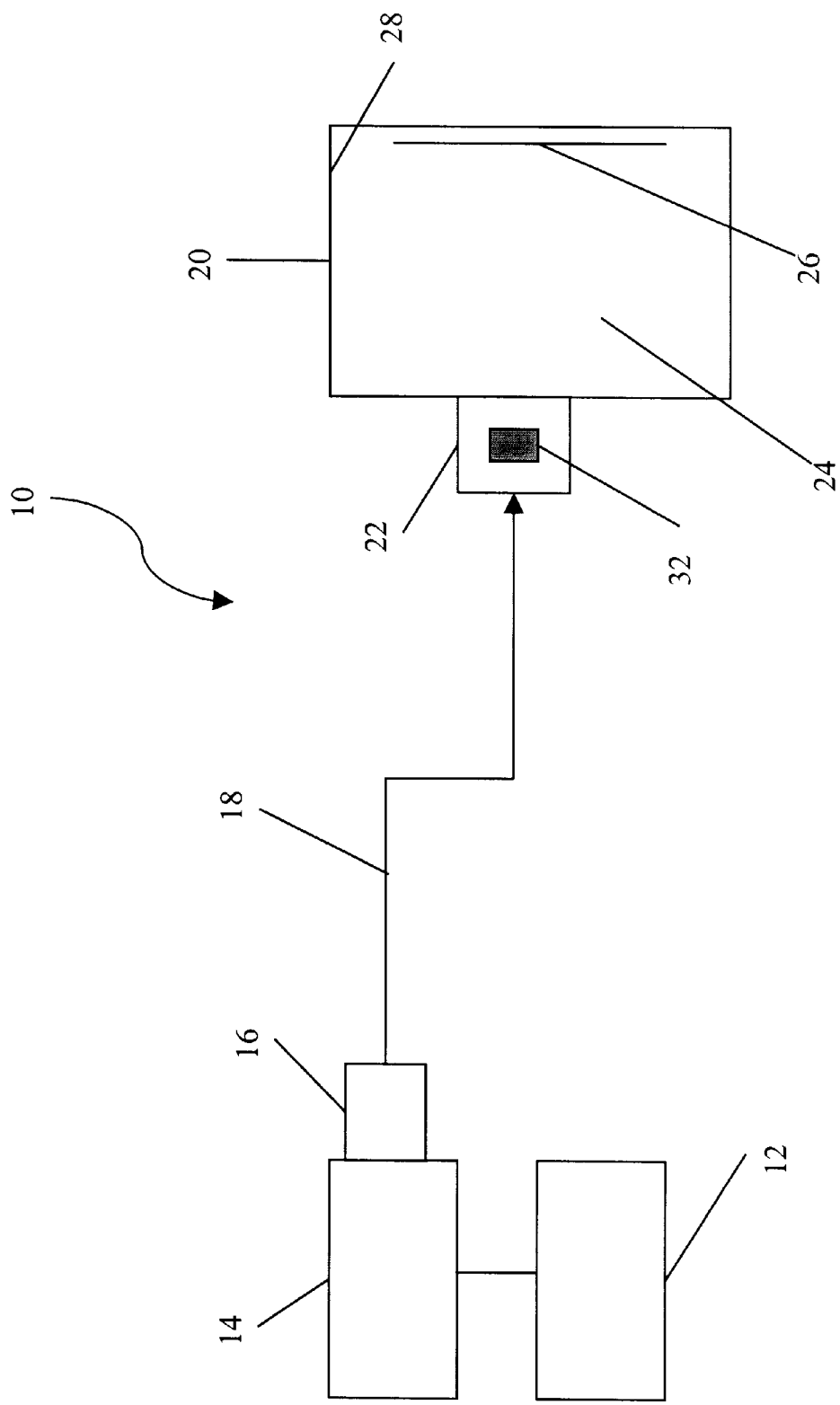
FIG. 1 is a schematic diagram of the complete UV appliance disinfection system.

In the following description, like reference characters designate like or corresponding parts throughout the several views. Also in the following description, it is to be understood that such terms as "forward," "rearward," "front," "back," "right," "left," "upwardly," "downwardly," and the like are words of convenience and are not to be construed as limiting terms.

Referring now to the drawings in general, the illustrations are for the purpose of describing a preferred embodiment of the invention and are not intended to limit the invention thereto. FIG. 1 shows a schematic diagram of a UV appliance disinfection system, generally described as 10. In the preferred embodiment, a power supply 12 powers a UV light source 14. UV light generated by the UV light source is focused and controlled by the means of optical components connected to the UV light source, or source optics 16 into at least one UV transmission line 18 that connects to the appliance 20 at a portal 22, which may alternatively be at least one portal if more than one light input is desired, thus transmitting UV light to the appliance. The appliance portal is equipped with optical components, or portal optics, 32 that control the UV light in order to enhance the disinfection of the appliance interior 24. The appliance interior can be equipped with UV reflective interior optical components, or interior optics, 26 or composed of a UV reflective interior surface or coating 28. Additionally, the interior surface of the appliance may contain a photocatalyst that degrades compounds contacting the interior surface of the appliance. For longevity as well as UV reflectivity, the interior surfaces may be made of stainless steel. Alternatively, other UV reflective materials may be used. Additionally, the contribution of the reflectance of internal surfaces to the efficacy of the system can be capitalized upon by incorporating UV-reflective materials and reflection-enhance design into the appliance. These same surfaces can also be manufactured such that they incorporate photocatalysts. Moreover, additional surfaces to support photocatalyst and enhance reflectance may be added to the reservoir or VRC system. Thus, an integrated 2 and 3-dimensional design that incorporates UV-reflectant materials, UV-reflectant design, photocatalysts, and additional photocatalyst and reflectant surfaces will greatly enhance the efficacy of the system.

While generally regarding the UV light source and configuration thereof, the preferred embodiment contains a UV light source that is remotely connectable to the appliance via at least on fiber optic transmission line. An alternate preferred embodiment contains a UV light source built into the appliance. Additionally, the preferred embodiment of the present invention includes at least one optical component positioned between the UV light source and the UV light source system output point. Advantageously, the use of optical components enables the system to maximize the intensity, focus, and control of the UV light rays at the output for any given UV light source or lamp. Also, optical components, including but not limited to reflectors, shutters, lenses, splitters, mirrors, rigid and flexible light guides, homogenizer or mixing rods, manifolds and other couplers, filters, color wheels, and the like, can be utilized in combination to achieve the desired control and output, as set forth in U.S. Pat. Nos. 6,027,237; 5,917,986; 5,911,020; 5,892,867; 5,862,277; 5,857,041; 5,832,151; 5,790,725; 5,790,723; 5,751,870; 5,708,737; 5,706,376; 5,682,448; 5,661,828; 5,559,911; D417,920, which are commonly owned by the assignee of the present invention, and which are incorporated herein by reference in their entirety. Additionally, optical component such as gratings, dichroic filters, focalizers, gradient lenses, gradient reflectors, off-axis lenses, and off-axis reflectors may be used. All UV transmissive optical components are made of UV-transmissive material and all UV-reflective optical components are made of UV-reflective material. The fiber optic lines may include glass fibers, acrylic fibers, liquid core fibers, core sheath fibers, or a combination of fibers.

With regard to lenses, several embodiments are envisioned. Imaging lenses, such as a parabolic lens, and non-imaging lenses, such as gradient lenses, may be used. A gradient lens collects light through a collecting opening and focuses it to an area smaller than the area of the collecting opening. This concentration is accomplished by changing the index of refraction of the lens along the axis of light transmission in a continuous or semi-continuous fashion, such that the light is "funneled" to the focus area by refraction. An example of gradient lens technology is the Gradium® Lens manufactured by Solaria Corporation. Alternatively, a toroidal reflector, as described in U.S. Pat. No. 5,836,667, is used. In this embodiment, a UV radiation source, such as an arc lamp, is located at a point displaced from the optical axis of a concave toroidal reflecting surface. The concave primary reflector focuses the radiation from the source at an off-axis image point that is displaced from the optical axis. The use of a toroidal reflecting surface enhances the collection efficiency into a small target, such as an optical fiber, relative to a spherical reflecting surface by substantially reducing aberrations caused by the off-axis geometry. A second concave reflector is placed opposite to the first reflector to enhance further the total flux collected by a small target.

Additionally, more than one reflector may be used with a lamp. For example, dual reflectors or three or more reflectors, as taught in U.S. Pat. Nos. 5,706,376 and 5,862,277, may be incorporated into the preferred embodiment.

Notably, any number of lamps including low pressure, medium pressure, high pressure, and ultra high-pressure lamps, which are made of various materials, e.g., most commonly mercury (Hg) can be used with the system configuration according to the present invention, depending upon the fluid or influent characteristics and flow rates through the system. Furthermore, while high and ultra high pressure lamps have not been used commercially to date by any prior art system, predominantly because of the low energy efficiency associated with them and the lack of capacity for prior art design and configuration formulas to include high pressure UV lamps, the present invention is advantageously suited to accommodate medium to high to ultra high pressure lamps, all of which can be metal, halogen, and a combination metal halide. Additionally, spectral calibration lamps, electrodeless lamps, and the like can be used.

In particular, a preferred embodiment according to the present invention employs a pencil-type spectral calibration lamp. These lamps are compact and offer narrow, intense emissions. Their average intensity is constant and reproducible. They have a longer life relative to other high wattage lamps. Hg (Ar) lamps of this type are generally insensitive to temperature and require only a two-minute warm-up for the mercury vapor to dominate the discharge, then 30 minutes for complete stabilization.

A Hg (Ar) UV lamp, which is presently commercially available and supplied by ORIEL Instruments, is used in the preferred embodiment according to the present invention. The ORIEL Hg(Ar) lamp, model 6035, emits UV radiation at 254 nm. When operated at 15 mA using a DC power supply, this lamp emits 74 microwatt/cm2 of 254 nm radiation at 25 cm from the source.

Another preferred embodiment of the system according to the present invention uses a light pump as a source of UV light. With this system, the number of lamps necessary to treat a given number of appliances can be reduced. Also, the lamps are not susceptible to fouling, since they are not immersed in the fluid to be disinfected. Additionally, the design of the present invention allows for a significant reduction in heat in the appliance. Furthermore, the maintenance and servicing is greatly simplified.

Another preferred embodiment according to the present invention employs medium to high-pressure UV lamps, more preferably high-pressure UV lamps.

In one embodiment according to the present invention, the UV light source is a Fusion RF UV lamp, which is presently commercially available and supplied by Fusion UV Systems, Inc. This fusion lamp has a spectrum like a low-pressure lamp, having very strong UVB&C availability and output, but is a high power lamp having approximately 200 W/cm. Significantly, as set forth in the foregoing, no prior art teaches or suggests the use of high pressure lamps, in fact, all standard formulas, including those developed by Dr. George Tchobanoglous, for system design and operation use low pressure lamps.

The present invention advantageously includes all of the above features, in particular because the UV lamps are separated from the appliance and include light delivery system that incorporates optical components. Without the use of optical components in combination with the UV light source, the intensity of the light could not be effectively focused, directed, and controlled to provide an efficacious disinfection because the UV dosage entering the appliance would not be great enough to sterilize the microorganisms.

The several advantages of this system include the fact that the remote lamp does not require as extensive cleaning maintenance to remove fouling as a lamp in the interior of the appliance may.

Additionally, this system allows for the lamp arrangement beneficially extends the lamp life thereby providing a longer replacement time or lamp life cycle. Since the lamp life is degraded by turning it off and on, the system can be constructed and configured to allow the reservoir to be significantly depleted before restarting the lamp (e.g., where a purified water reservoir or tank is used, the lamp activity can be controlled, preprogrammed, and otherwise regulated to correspond to the tank water size and water level. Depending on the size of the reservoir, and the number of people using the system (as measured in demanded or used gallons/day), the lamp is arranged, configured, and programmed to run intermittently, e.g., for an hour or so per day. In this way, a lamp continuous operation life of about a month could be extended to perhaps a year, depending upon the particular characteristics and specifications of the system, including water characteristics.

Thus, as can be seen from the advantages of this preferred embodiment according to the present invention, the maintenance required for this preferred embodiment according to the present invention is significantly reduce.

Portal Optics

In the preferred embodiment, at least one portal optic is positioned at the portal opening of the appliance, between the portal opening and the interior of the appliance. The function of the at least one portal optic is to control the distribution of UV light in the appliance in order to enhance the UV disinfecting capacity of the system. The portal optics may be similar to those described for the source optics, including but not limited to reflectors, shutters, lenses, splitters, mirrors, rigid and flexible light guides, homogenizer or mixing rods, manifolds and other couplers, filters, color wheels, and the like, can be utilized in combination to achieve the desired control and output, as set forth in U.S. Pat. Nos. 6,027,237; 5,917,986; 5,911,020; 5,892,867; 5,862,277; 5,857,041; 5,832,151; 5,790,725; 5,790,723; 5,751,870; 5,708,737; 5,706,376; 5,682,448; 5,661,828; 5,559,911; D417,920 and co-pending application Ser. Nos. 09/523,609 and 09/587,678 which are commonly owned by the assignee of the present invention, and which are incorporated herein by reference in their entirety. Additionally, optical component such as gratings, dichroic filters, focalizers, gradient lenses, and off-axis reflectors may be used. All UV transmissive optical components are made of UV-transmissive material and all UV-reflective optical components are made of UV-reflective material. These optics may extend into the appliance. For example, fiber optic transmission lines may be used to route UV light to the various areas of the appliance. The fiber optic lines may include glass fibers, acrylic fibers, liquid core fibers, core sheath fibers, or a combination of fibers.

UV Dose Zones

Advantageously, these appliances have several UV dose zones (not shown) established within them, these UV dose zones being variable, i.e. the greater the distance from the light source introduction, the lesser the UV light intensity at a particular region or area. The first zone is the light source system exit UV dose zone, which occurs at the light source system and air interface. Then next zone is the air interior UV dose zone, which occurs in the interior of the appliance. This zone may be an air zone or a vapor zone, depending on the function of the appliance and when the appliance is irradiated. The last zone is the UV surface dose zone, which occurs at the interior surface of the appliance.

Interior Surface

The interior surface of the appliance may possess photocatalytic properties such that certain reactions are catalyzed in the vicinity of the interior surface. For example, $TiO_2$ may be incorporated into the interface plate that is made of glass or other appropriate material. When such a surface is irradiated with activating light, fatty acids and other organic chemicals are chemically reduced, resulting in degradation to smaller volatile products such as methane, ethane, etc. Additionally, nitrate ion is reduced to elemental nitrogen in such a system. Thus, the incorporation of $TiO_2$ or other photocatalytic material into the interior surface with subsequent irradiation by activating wavelengths reduces the levels of two potential human toxins—organic chemicals and nitrate ion. Advantageously, the disinfected appliance is completely free from microorganisms without requiring the addition of chemicals or other additives that would increase the chemical residue on the surface of the appliance.

Such a system of UV disinfection can be easily integrated into the appliance function cycle by activating the UV light source or allowing irradiation of the appliance interior at a predetermined time in an appliance function cycle. Alternately, the UV disinfection system may be manually activated when desired.

Certain modifications and improvements will occur to those skilled in the art upon a reading of the foregoing description. By way of example, various optical components are used depending upon the particular UV light source or lamp selection for a given system. Moreover, a wide range of applications are contemplated within the scope of the present invention, including application of the UV fluid disinfectant system and method to appliance involved in washing, rinsing, storing, fluid dispensing, and combinations thereof. By way of example, the disinfection of appliances, includes, but is not limited to, ambient temperature and chilled water tanks, refrigerators, water fountains, water towers, beverage makers, beverage dispensers, dishwashers, water heaters, washing machines, bathtubs, showers, toilets, and water pumps. These appliances may be for commercial or household use. Additionally, appliances not normally associated with food consumption, but that can harbor pathogens, may be fitted with a UV disinfectant system and method according to the present invention. By way of example and not of limitation, vacuum cleaners, air conditioners, storage containers, and the like may be fitted with a UV disinfection system and method according to the present invention in order to disinfect or maintain the microbial purity of the appliance or the emissions therefrom.

These multiple points of application may also be connected to a single light source, such as a light pump, by light guides. Such an arrangement would eliminate the need for a lamp or light source at every point of application. Because it may not be necessary to continuously irradiate each point of application, such an arrangement would allow the same size lamp as would be require for a single application to service multiple applications intermittently and/or on demand, thus utilizing the lamp more efficiently. Additionally, placing the lamp exterior to the tank reduces the risk of glass and/or mercury contaminating the appliance should the lamp or lamp housing break. An additional benefit to such a configuration is that filters previously required in immersion-type systems to prevent such contamination are no longer required.

All modifications and improvements have been deleted herein for the sake of conciseness and readability but are properly within the scope of the following claims.

I claim:

1. An ultraviolet disinfection (UV) system for appliances, the system comprising
   at least one UV light-ready appliance having at least one portal in the appliance for receiving UV light input from at least one light source, the at least one light source removably connected to the at least one UV light-ready appliance via a connector at the portal, the at least one light source positioned to provide a focused, controllable UV light output that has at least one UV dose zone for providing effective sterilization of microorganisms and disinfection within an interior of the appliance.

2. The UV system according to claim 1, wherein the at least one light source is built into the appliance.

3. The UV system according to claim 1, wherein the at least one light source is remotely connectably to the appliance via at least one fiber optic transmission lines, wherein the fiber optic transmission lines have a first end connected to the housing output such that the UV light output from the at least one light source passes through the fiber optic transmission lines and exiting from a second end such that the UV light output exiting the fiber optic transmission lines is projected into the interior of the appliance.

4. The UV system according to claim 3, wherein the at least one light source is a light pump.

5. The UV system according to claim 1, wherein the at least one light source is a UV lamp.

6. The UV system according to claim 3, wherein the at least one light source includes at least one source optical component positioned between the at least one light source and the fiber optic transmission lines.

7. The UV system according to claim 6, wherein the at least one source optical component is selected from the group consisting of reflectors, shutters, lenses, splitters, focalizers, mirrors, rigid and flexible light guides, homogenizer, mixing rods, manifolds and other couplers, filters, gratings, diffracters, gradient lenses, color wheels, off-axis reflectors, cascading reflectors, splitting reflectors, and combinations thereof.

8. The UV system according to claim 3, wherein the fiberoptic lines include acrylic fibers.

9. The UV system according to claim 3, wherein the fiberoptic lines include glass fibers.

10. The UV system according to claim 3, wherein the fiberoptic lines include liquid core fibers.

11. The UV system according to claim 3, wherein the fiberoptic lines include hollow core fibers.

12. The UV system according to claim 3, wherein the fiberoptic lines include core-sheath fibers.

13. The UV system, according to claim 1, wherein the at least one light source is one lamp.

14. The UV system according to claim 3, wherein the at least one light source is a spectral calibration lamp.

15. The UV system according to claim 3, wherein the at least one light source is an electrodeless lamp.

16. The UV system according to claim 3, wherein the at least one light source is a mercury halide lamp.

17. The UV system according to claim 6, wherein at least one source optical component is UV transmissive.

18. The UV system according to claim 6, wherein at least one source optical component is UV reflective.

19. The UV system according to claim 1, further including at least one portal optical component positioned between the portal opening and the interior of the appliance.

20. The UV system according to claim 1, wherein the at least one portal optical component is UV transmissive.

21. The UV system according to claim 1, wherein the at least one portal optical component is UV reflective.

22. The UV system according to claim 1, wherein the at least one portal optical component is selected from the group consisting of reflectors, shutters, lenses, splitters, focalizers, mirrors, rigid and flexible light guides, homogenizer, mixing rods, manifolds, couplers, filters, gratings, diffracters, color wheels, and combinations thereof.

23. The UV system according to claim 1, wherein the interior of the applicance is UV reflective.

24. The UV system according to claim 1, wherein the interior of the applicance has interior surfaces include materials that are UV reflective.

25. The UV system according to claim 24, wherein the interior surfaces are coated with a UV reflective material.

26. The UV system according to claim 24, wherein the interior surfaces are stainless steel.

27. The UV system according to claim 23, wherein the interior of the applicance includes interior optics that are attached to the interior surfaces.

28. The UV system according to claim 27, wherein the interior optics are UV reflectors.

29. The UV system according to claim 1, wherein the interior surfaces of the appliance includes at least one catalytic material for producing a photocatalytic reaction when activated by at least one UV dose zone.

30. The UV system according to claim 29, wherein the at least one catalytic material includes TiO2.

31. The UV system according to claim 1, wherein the UV-ready appliance is capable of being installed into a building by being connected at the portal to the at least one light source through the fiber optic transmission lines, which are removably attached via the connector.

32. The UV system according to claim 1, wherein the at least one appliance is selected from the group consisting of dishwashers, washing machines, refrigerators, ice-making machines, freezers, drinking fluid dispensers, dryers, and combinations thereof.

33. An ultraviolet disinfection (UV) system for appliances, the system comprising at least one light source positioned within a housing that is external to at least one appliance and capable of being connected to the at least one appliance via at least one connector and connected to a power source for producing a UV light output from the housing, the system including at least one source optical component positioned between the at least one light source and the UV light output from the housing, thereby producing a focused, controllable UV light output that has at least one UV dose zone for providing effective sterilization of microorganisms within the at least one appliance.

34. The UV system according to claim 33, wherein the system is adaptable to be removably connected to fiber optic transmission lines, such that a multiplicity of appliances may be positioned to function at a corresponding multiplicity locations within a building to provide UV disinfection at multiplicity of appliances selectively and simultaneously.

35. The UV system according to claim 33, wherein the at least one source optical component is selected from the group consisting of reflectors, shutters, lenses, splitters, focalizers, mirrors, rigid and flexible light guides, homogenizer, mixing rods, manifolds, couplers, filters, gratings, diffracters, color wheels, and combinations thereof.

36. The UV system according to claim 33, wherein the at least one light source is a light pump.

37. The UV system according to claim 33, wherein the at least one light source is a UV lamp.

38. The UV system according to claim 33, wherein the at least one light source is a spectral calibration lamp.

39. The UV system according to claim 33, wherein the at least one light source is an electrodeless lamp.

40. The UV system according to claim 33, wherein the at least one light source is a mercury halide lamp.

41. The UV system according to claim 34, wherein the fiber optic transmission lines, are UV transmissive.

42. The UV system according to claim 34, wherein the fiberoptic lines include acrylic fibers.

43. The UV system according to claim 34, wherein the fiberoptic lines include glass fibers.

44. The UV system according to claim 34, wherein the fiberoptic lines include liquid core fibers.

45. The UV system according to claim 34, wherein the fiberoptic lines include hollow core fibers.

46. The UV system according to claim 34, wherein the fiberoptic lines include core-sheath fibers.

47. A method for providing ultraviolet disinfection (UV) within appliances, the method comprising the steps of:

providing at least one UV light-ready appliance having at least one portal in the appliance for receiving UV light input from at least one light source, the at least one light source removably connected to the at least one UV light-ready appliance via a connector at the portal, the at least one light source positioned to provide a focused, controllable UV light output that has at least one UV dose zone for providing effective sterilization of microorganisms and disinfection within an interior of the appliance;

activating the at least one light source at a predetermined time in an appliance function cycle;

exposing the interior surfaces and interior of the appliance to at least one UV dose zone;

sterilizing microorganisms existing within the interior of the appliance and all materials contained within the interior of the appliance;

deactivating the at least one light source.

48. The method according to claim 47, further including the steps of manually activating the at least one light source.

49. The method according to claim 47, wherein the activation occurs during the appliance function selected from the group consisting of washing, rinsing, storing, fluid dispensing, and combinations thereof.

50. The method according to claim 47, wherein the interior 3-dimensional structure of the provided appliance is designed such that it enhances the reflection of light.

* * * * *